(12) United States Patent
Hehn et al.

(10) Patent No.: US 8,513,020 B2
(45) Date of Patent: Aug. 20, 2013

(54) CORROSION TESTING APPARATUS AND METHODS

(75) Inventors: Lucien Hehn, Spring, TX (US); Kevin J. Wyble, Spring, TX (US); Kenneth E. Casner, Jr., Calumet City, IL (US); Kenneth E. Casner, Sr., Calumet City, IL (US); Joseph Casner, Dyer, IN (US); George M. Waid, Taft, TN (US)

(73) Assignee: National Oilwell Varco, L.P., Houston, TX (US)

( * ) Notice: Subject to any disclaimer, the term of this patent is extended or adjusted under 35 U.S.C. 154(b) by 247 days.

(21) Appl. No.: 12/961,901

(22) Filed: Dec. 7, 2010

(65) Prior Publication Data
US 2011/0136239 A1    Jun. 9, 2011

Related U.S. Application Data

(60) Provisional application No. 61/267,600, filed on Dec. 8, 2009.

(51) Int. Cl.
| G01N 17/04 | (2006.01) |
| G01N 3/20 | (2006.01) |
| G01N 3/04 | (2006.01) |
| G01N 33/20 | (2006.01) |

(52) U.S. Cl.
USPC .............. 436/6; 73/53.01; 73/61.62; 73/86; 73/104; 73/799; 73/819; 73/852; 73/856; 73/859; 422/53

(58) Field of Classification Search
USPC .............. 73/53.01, 61.62, 86, 104, 799, 819, 73/856, 859, 852, 788; 422/53; 436/6
See application file for complete search history.

(56) References Cited

U.S. PATENT DOCUMENTS

| 1,332,491 | A | * | 3/1920 | Francesco | 73/796 |
| 2,338,338 | A | * | 1/1944 | Kieckhefer | 73/854 |
| 2,404,584 | A | * | 7/1946 | Liska et al. | 374/52 |
| 2,504,985 | A | * | 4/1950 | Kallas et al. | 374/52 |

(Continued)

FOREIGN PATENT DOCUMENTS

| JP | 3-229133 | * 10/1991 |
| JP | 10-185798 | * 7/1998 |
| KR | 20-1991-0004288 Y1 | 4/1991 |

OTHER PUBLICATIONS

Hogland, R. G. et al, Journal of the American Ceramic Society 1976, 59, 189-192.*

(Continued)

*Primary Examiner* — Arlen Soderquist
(74) *Attorney, Agent, or Firm* — Conley Rose, P.C.

(57) ABSTRACT

A system for sulfide stress cracking testing comprises an enclosed testing chamber including a fluid bath comprising a liquid saturated with hydrogen sulfide gas. In addition, the system comprises a test fixture disposed in the testing chamber and at least partially submerged in the fluid bath. The test fixture includes a housing having an internal chamber in fluid communication with the fluid bath and a test assembly disposed in the internal chamber. The test assembly comprises a first upper support and a second upper support, a first lower support and a second lower support, and a first platen engaging each of the upper supports and adapted to transfer an applied vertical load to the upper supports. Further, the system comprises a test specimen mounted in the test assembly between the upper supports and the lower supports.

19 Claims, 9 Drawing Sheets

(56) References Cited

U.S. PATENT DOCUMENTS

| | | | | |
|---|---|---|---|---|
| 2,506,048 A * | 5/1950 | Van Den Akker | | 73/852 |
| 2,664,744 A * | 1/1954 | Bilhartz et al. | | 422/53 |
| 2,670,624 A * | 3/1954 | Faris, Jr. et al. | | 374/52 |
| 3,130,579 A * | 4/1964 | Cram et al. | | 73/842 |
| 3,142,174 A * | 7/1964 | Baker | | 73/852 |
| 3,323,356 A * | 6/1967 | Arias | | 73/852 |
| 3,324,714 A * | 6/1967 | Albert et al. | | 73/853 |
| 3,500,679 A * | 3/1970 | Smith | | 73/850 |
| 4,033,181 A * | 7/1977 | Oeser | | 73/800 |
| 4,213,349 A * | 7/1980 | Miura | | 73/847 |
| 4,222,772 A * | 9/1980 | Sogo et al. | | 420/103 |
| 4,461,018 A * | 7/1984 | Ice et al. | | 378/84 |
| 4,583,407 A * | 4/1986 | LeGrand et al. | | 73/762 |
| 4,625,563 A * | 12/1986 | Dawson et al. | | 73/850 |
| 4,677,856 A * | 7/1987 | Fischer | | 73/850 |
| 4,730,498 A * | 3/1988 | Blanch | | 73/852 |
| 4,735,093 A * | 4/1988 | Burchill et al. | | 73/854 |
| 4,763,529 A * | 8/1988 | Leonard et al. | | 73/852 |
| 4,770,703 A * | 9/1988 | Tarutani et al. | | 75/246 |
| 4,859,415 A * | 8/1989 | Shida et al. | | 420/417 |
| 4,875,376 A * | 10/1989 | Fischer | | 73/852 |
| 4,941,359 A * | 7/1990 | Quinn et al. | | 73/851 |
| 4,976,152 A * | 12/1990 | McKinley et al. | | 73/852 |
| 4,986,132 A * | 1/1991 | Calomino | | 73/852 |
| 5,005,423 A * | 4/1991 | Poormon | | 73/799 |
| 5,156,807 A * | 10/1992 | Nagata et al. | | 420/417 |
| 5,178,017 A * | 1/1993 | Dinzburg | | 73/849 |
| 5,187,987 A * | 2/1993 | Anderson et al. | | 73/852 |
| 5,231,882 A * | 8/1993 | Bertele et al. | | 73/852 |
| 5,277,069 A * | 1/1994 | Cussac et al. | | 73/853 |
| 5,415,894 A * | 5/1995 | McGarry | | 427/386 |
| 5,448,917 A * | 9/1995 | Maciejewski | | 73/812 |
| 5,505,095 A * | 4/1996 | Raymond | | 73/853 |
| 5,549,007 A * | 8/1996 | Raymond | | 73/856 |
| 5,585,570 A * | 12/1996 | Raymond | | 73/851 |
| 5,598,738 A * | 2/1997 | Buescher et al. | | 73/761 |
| 5,847,283 A * | 12/1998 | Finot et al. | | 73/812 |
| 5,913,246 A * | 6/1999 | Simonelli et al. | | 73/808 |
| 6,042,782 A * | 3/2000 | Murata et al. | | 420/109 |
| 6,120,908 A * | 9/2000 | Papanu et al. | | 428/429 |
| 6,171,933 B1* | 1/2001 | Xu et al. | | 438/462 |
| 6,234,029 B1* | 5/2001 | Liang et al. | | 73/850 |
| 6,332,364 B1* | 12/2001 | Buschmann et al. | | 73/788 |
| 6,379,821 B2* | 4/2002 | Kushida et al. | | 428/685 |
| 6,573,471 B1* | 6/2003 | Kuriyama et al. | | 219/121.14 |
| 6,609,408 B2* | 8/2003 | Chen et al. | | 73/7 |
| 6,652,617 B2* | 11/2003 | Maili et al. | | 75/243 |
| 6,782,921 B1* | 8/2004 | Tsuru et al. | | 138/142 |
| 6,790,707 B1* | 9/2004 | Cui | | 438/114 |
| 6,918,306 B1* | 7/2005 | Cavallaro et al. | | 73/849 |
| 7,082,992 B2* | 8/2006 | Amaya et al. | | 166/207 |
| 7,520,178 B2* | 4/2009 | Ohno et al. | | 73/799 |
| 7,574,922 B2* | 8/2009 | Doleski et al. | | 73/841 |
| 7,579,288 B2* | 8/2009 | Kwon et al. | | 438/800 |
| 8,096,191 B2* | 1/2012 | Ladani et al. | | 73/856 |
| 8,177,953 B2* | 5/2012 | Nardi et al. | | 205/81 |
| 8,303,708 B2* | 11/2012 | Rigaud et al. | | 106/713 |
| 2001/0030004 A1* | 10/2001 | Kushida et al. | | 148/325 |
| 2003/0047013 A1* | 3/2003 | Chen et al. | | 73/866 |
| 2008/0115597 A1* | 5/2008 | Ohno et al. | | 73/865.8 |
| 2010/0147423 A1* | 6/2010 | Siller et al. | | 148/579 |
| 2010/0147694 A1* | 6/2010 | Nardi et al. | | 205/81 |

OTHER PUBLICATIONS

Stromswold, E. I. et al, Engineering Fracture Mechanics 1992, 41, 309-320.*

Gilchrist, M. D. et al, Composites Science and Technology 1996, 56, 37-53.*

Lin, C.-K. et al, Jopurnal of the American Ceramic Society 1997, 80, 2382-2394.*

Schuecker, C. et al, Composites Science and Technology 2000, 60, 2137-2146.*

Megel, M. et al, Composites Science and Technology 2001, 61, 231-246.*

Wiedemann, R. et al, Advanced Engineering Materials 2001, 3, 865-870.*

Heitkemper M. et al, International Journal of Fatigue 2003, 25, 101-106.*

Feraboli, P. et al, Composites: Part A 2003, 34, 1265-1271.*

Lund, E. et al, Review of Scientific Instruments 2004, 75, 4960-4967.*

Turnbull, A. et al, Corrosion Engineering, Science and Technology 2005, 40, 103-110.*

Mendels, D.-A. et al, Philosophical Magazine 2005, 85, 1765-1782.*

Huang, Z. et al, Engineering Fracture Mechanics 2005, 72, 2584-2601.*

Yamazaki, Y. et al, Surface & Coatings Technology 2006, 201, 744-754.*

Belingardi, G. et al, Composites: Part A 2007, 38, 1183-1191.*

Scholz, A. et al, International Journal of Fatigue 2008, 30, 357-362.*

Wang, B. et al, Microelectronic Engineering 2008, 85, 477-485.*

Bertolini, J. et al, Composite Structures 2008, 86, 233-242.*

Richter, J. et al, Review of Scientific Intruments 2008, 79, 044703 (11 pages).*

Cho, C.-H., Current Applied Physics 2009, 9, 538-545.*

Kasuya, T. et al, Science and Technology of Welding & Joining 1998, 3, 25-32.*

Azarmi, F. et al, Journal of Materials Science 2009, 44, 2836-2843.*

Malumbela, G. et al, Construction and Building Materials 2009, 23, 3346-3351.*

Haridarshan Enterprise SSC Temperature Pressure Vessels and 4-Point Bed SSC Test Products; retrieved from: http://www.hicoindia.com/coating-corrosion.html#cte) (15 p.).

NACE, "Standard Test Method: Laboratory Testing of Metals for Resistance to Sulfide Stress Cracking and Stress Corrosion Cracking in H2S Environments", ANSI/NACE Standard TM0177-96, Item No. 21212, Sep. 1997.

European Federation of Corrosion Working Party 13—Corrosion in Oil & Gas dated Sep. 10, 2009; retrieved from: http://www.efcweb.org/efcweb_media/Downloads/EFC+WP13/WP13+MOM+Nice+2009.pdf) (126 p.).

Haridarshan Enterprise SSC Temperature Pressure Vessels and 4-Point Bed SSC Test Products; retrieved from: http://www.hicoindia.com/coating-corrosion.html#cte) (15 p.), Copyright 2009.

* cited by examiner

CORROSION TESTING APPARATUS AND METHODS

CROSS-REFERENCE TO RELATED APPLICATIONS

This application claims benefit of U.S. provisional patent application Ser. No. 61/267,600 filed Dec. 8, 2009, and entitled "Corrosion Testing System," which is hereby incorporated herein by reference in its entirety.

STATEMENT REGARDING FEDERALLY SPONSORED RESEARCH OR DEVELOPMENT

Not applicable.

BACKGROUND

1. Field of the Invention

The invention relates generally to corrosion testing. More particularly, the invention relates to corrosion testing welded connections. Still more particularly, the present invention relates to testing welded steel joints for resistance to sulfide stress cracking.

2. Background of the Technology

Sulfide stress cracking (SSC) is a form of corrosive hydrogen embrittlement that can lead to weakening, fracturing, and cracking of susceptible metal alloys such as steel. This condition is called SSC because it requires the combination of both stress and hydrogen sulfide acting together on the susceptible metal alloy. Specifically, the metal alloy reacts with hydrogen sulfide ($H_2S$) to form metal sulfides and atomic hydrogen as corrosion byproducts. The atomic hydrogen product combines to form hydrogen gas ($H_2$) at the surface of the metal or diffuses into the metal matrix.

SSC has particular importance in the gas and oil industry since the materials being processed (e.g., natural gas and crude oil) often contain considerable amount of hydrogen sulfide. Specifically, exposure to hydrogen sulfide and associated SSC can cause catastrophic failure in otherwise high integrity steel.

To mitigate this problem, standardized testing procedures were developed by the National Association of Corrosion Engineers (NACE) and others. For instance, equipment that comes in contact with hydrogen sulfide gas can be rated for sour service with adherence to NACE MR0175 and NACE TM0177 for oil and gas production environments or NACE MR0103 for oil and gas refining environments. These standardized tests provide assurance that a given steel grade (and accompanying processing parameters) would be safe for use in hydrogen sulfide rich environments up to a particular stress level. A typical test includes subjecting a test sample or specimen to a high tensile load in a liquid saturated with hydrogen sulfide gas for 30 days. In general, a test sample is considered to pass the test if the sample survived the 30 day test without fracturing or showing visible cracking.

In the oil and gas industry, many types of steel tubulars designed for subsurface use (e.g., drill pipe) are welded together with friction-type welds. The area immediately surrounding each weld (approximately 0.50-0.75 inches laterally to either side of the weld) is now being required by some drillers to be demonstrated to be safe from SSC in service. Consequently, the integrity of weld areas of tubulars subjected hydrogen sulfide gas is now of principle concern in the oil and gas industry. Conventional test procedures and standards outlined by NACE do not adequately address or cover such friction-type welds. For example, NACE document TM0177 is the authoritative guideline providing specifications for SSC testing methods, and outlines specifications for several types of test fixtures as well as other parameters for carrying out SSC testing of steel. However, NACE document TM0177 does not specifically address SSC testing of welds. Further, NACE document MR0175 is the authoritative guideline for the use of various steel alloys and fillet welds in sour environments (i.e., hydrogen sulfide rich environments), but addresses only fillet-type and butt welds. Fillet and butt welds are sufficiently different from friction-type welds that the guidelines in NACE document MR0175 are generally not extended to friction-type welds.

Accordingly, there remains a need in the art for apparatus and methods for testing the durability of friction welds between steel components subjected to stress in hydrogen sulfide rich environments. Such testing apparatus and methods would be particularly well-received if they were relatively easy to implement, repeatable and reuseable, and accurately reflected conditions encountered in field.

BRIEF SUMMARY OF THE DISCLOSURE

These and other needs in the art are addressed in one embodiment by a system for sulfide stress cracking testing. In an embodiment, the system comprises an enclosed testing chamber including a fluid bath comprising a liquid saturated with hydrogen sulfide gas. In addition, the system comprises a test fixture disposed in the testing chamber and at least partially submerged in the fluid bath. The test fixture includes a housing having an internal chamber in fluid communication with the fluid bath and a test assembly disposed in the internal chamber. The test assembly comprises a first upper support and a second upper support, a first lower support and a second lower support, and a first platen engaging each of the upper supports and adapted to transfer an applied vertical load to the upper supports. Further, the system comprises a test specimen mounted in the test assembly between the upper supports and the lower supports. The upper supports engaging an upper surface of the test specimen and the lower supports engaging a lower surface of the test specimen. The test specimen has a longitudinal axis, a first end, a second end opposite the first end, and includes a weld and a heat affected zone axially disposed between the first end and the second end. The first upper support is axially positioned between the weld and the first end and the second upper support is axially positioned between the weld and the second end. The first lower support is axially positioned between the first upper support and the first end and the second lower support is axially positioned between the second upper support and the second end.

These and other needs in the art are addressed in another embodiment by a method for corrosion testing a weld. In an embodiment, the method comprises (a) providing a test specimen having a longitudinal axis, a first end, a second end opposite the first end, and a weld axially positioned between the first end and the second. In addition, the method comprises (b) mounting the test specimen between a pair of upper supports and a pair of lower supports. Further, the method comprises (c) subjecting the test specimen to a four point bending test with the upper supports and the lower supports to induce tensile stress in the specimen along a lower surface of the specimen during. Still further, the method comprises (d) exposing the weld to hydrogen sulfide gas during (c).

Thus, embodiments described herein comprise a combination of features and advantages intended to address various shortcomings associated with certain prior devices, systems, and methods. The various characteristics described above, as well as other features, will be readily apparent to those skilled in the art upon reading the following detailed description, and by referring to the accompanying drawings.

BRIEF DESCRIPTION OF THE DRAWINGS

For a detailed description of the preferred embodiments of the invention, reference will now be made to the accompanying drawings in which.

DETAILED DESCRIPTION OF SOME OF THE PREFERRED EMBODIMENTS

Figure 1:
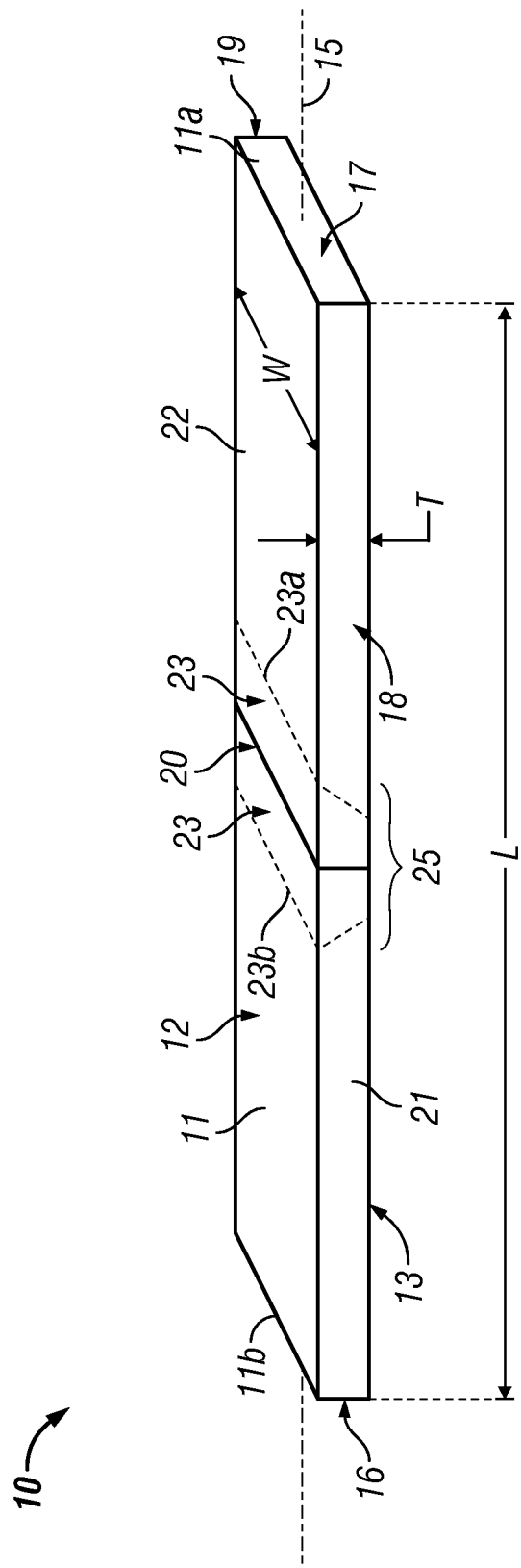
FIG. 1 is a perspective view of an embodiment of a welded specimen for SSC testing.

The following discussion is directed to various embodiments of the invention. Although one or more of these embodiments may be preferred, the embodiments disclosed should not be interpreted, or otherwise used, as limiting the scope of the disclosure, including the claims. In addition, one skilled in the art will understand that the following description has broad application, and the discussion of any embodiment is meant only to be exemplary of that embodiment, and not intended to intimate that the scope of the disclosure, including the claims, is limited to that embodiment.

Certain terms are used throughout the following description and claims to refer to particular features or components. As one skilled in the art will appreciate, different persons may refer to the same feature or component by different names. This document does not intend to distinguish between components or features that differ in name but not function. The drawing figures are not necessarily to scale. Certain features and components herein may be shown exaggerated in scale or in somewhat schematic form and some details of conventional elements may not be shown in interest of clarity and conciseness.

In the following discussion and in the claims, the terms "including" and "comprising" are used in an open-ended fashion, and thus should be interpreted to mean "including, but not limited to . . . ." Also, the term "couple" or "couples" is intended to mean either an indirect or direct connection. Thus, if a first device couples to a second device, that connection may be through a direct connection, or through an indirect connection via other devices, components, and connections. In addition, as used herein, the terms "axial" and "axially" generally mean along or parallel to an axis (e.g., longitudinal axis of a body or a port), and the terms "radial" and "radially" generally mean perpendicular to the axis. The terms "lateral" and "laterally" generally mean to the side of another feature or object.

Referring now to FIG. 1, an embodiment of a test specimen or sample 10 including a weld 20 for SSC testing is shown. Sample 10 has an elongate body 11 with a central or longitudinal axis 15, a first end 11a, and a second end 11b opposite first end 11a. In addition, body 11 has a planar upper surface 12 extending between ends 11a, b, a planar lower surface 13 parallel to upper surface 12 and extending between ends 11a, b, planar end surfaces 16, 17 extending vertically between upper and lower surfaces 12, 13 at ends 11a, b, respectively, and planar side surfaces 18, 19 extending vertically between upper and lower surfaces 12, 13. Body 11 has a length L measured axially between ends 11a, b, a thickness T measured perpendicularly from upper surface 12 to lower surface 13, and a width W measured perpendicularly from front surface 18 to rear surface 19. In this embodiment, body 11 has the general shape of an elongate rectangular bar since length L is greater than width W, and length L is greater than thickness T. For purposes of the four point bending tests described in more detail below, length L is preferably at least 20 times thickness T.

Sample 10 is formed from a first component 21 axially abutting and welded end-to-end to a second component 22 with weld 20. In this embodiment, weld 20 is a friction weld. However, in general, other types of welded connections and joints may be tested in accordance with the principles described herein.

Components 21, 22, and hence sample 10, are made from a material for which SSC testing is desired. Thus, for SSC testing of welds in steel, components 21, 22 will comprise pieces of steel that are welded together. In general, heat from the welding process and subsequent re-cooling alters the microstructure and properties of the base material immediately surrounding the weld, often referred to as the heat affected zone (HAZ). Thus, sample 10 includes a heat affected zone 23 immediately surrounding weld 20. Heat affected zone 23 extends along the entire length of weld 20 (i.e., between side surfaces 18, 19) and extends perpendicularly from weld 20 to heat affect zone boundaries 23a, b positioned axially (relative to axis 15) between weld 20 and each end 11a, b, respectively. For most welds (e.g., weld 20), the heat affected zone (e.g., heat affected zone 17) extends about 0.5 to 0.75 inches to either side of the weld. Thus, each boundary 23a, b will typically be positioned about 0.5 to 0.75 inches from weld 20.

Together, weld 20 and heat affected zone 23 define an area of interest 25 in sample 10 to be SSC tested. As will be described in more detail below, embodiments of testing apparatus and fixtures described herein are employed to simultaneously subject area of interest 25 to stress and hydrogen sulfide gas to test its resistance to SSC. Results from such tests may be used to grade and/or qualify weld 20 and the associated area of interest 25 for use in sour environments (i.e., environments rich in hydrogen sulfide gas).

Figure 2:
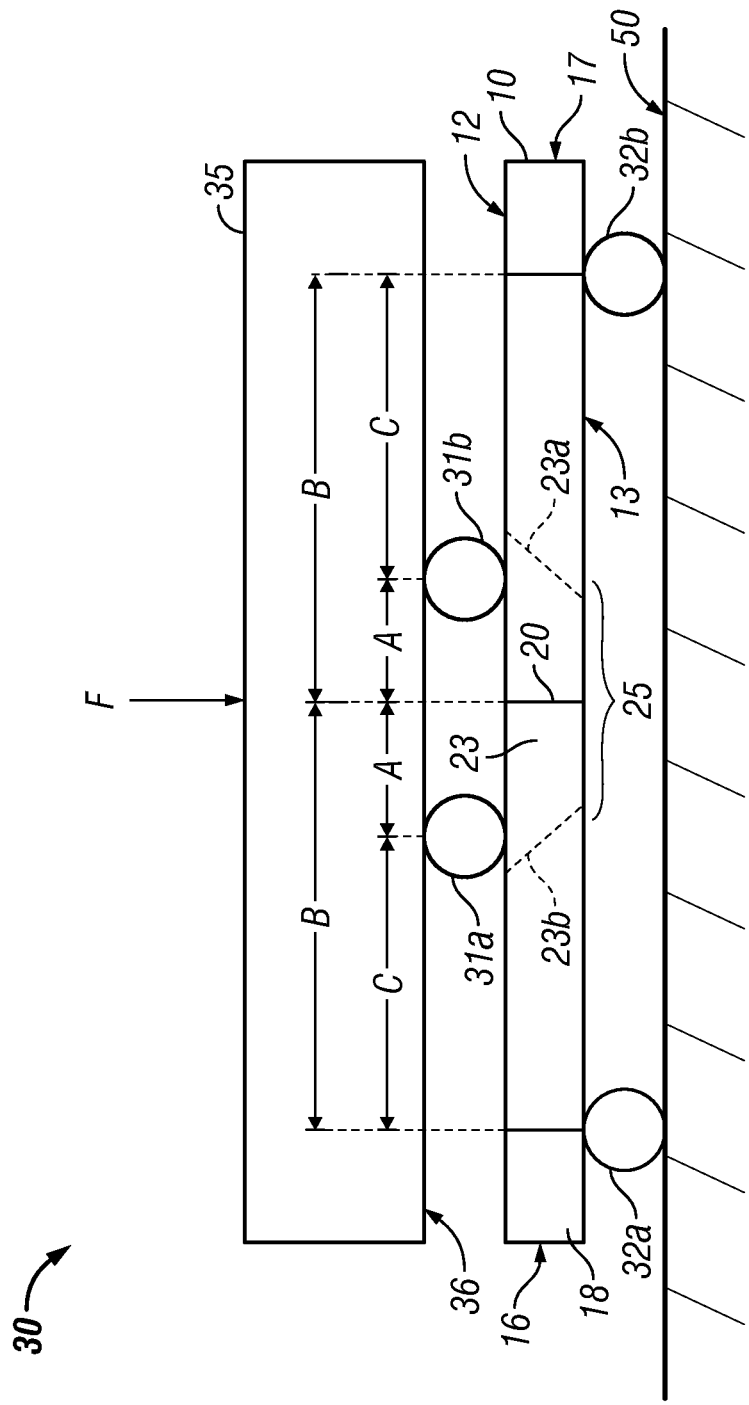
FIG. 2 is a front view of the specimen of FIG. 1 subjected to a four point bending test.

Referring now to FIG. 2, sample 10 is schematically shown being subjected to a four point bending test via a testing assembly 30. Testing assembly 30 includes a pair of upper force transfer members or supports 31a, b, a pair of lower force transfer members or supports 32a, b, and a force or press platen 35. Sample 10 is mounted between upper supports 31a, b and lower supports 32a, b. Upper supports 31a, b extend across upper surface 12 between surfaces 18, 19 and are oriented parallel to weld 20 and perpendicular to axis 15 in top view. In particular, supports 31a, b are evenly axially spaced (relative to axis 15) to either side of weld 20 by a distance A measured perpendicularly from weld 20. Supports 31a, b are preferably positioned at or proximal heat affected zone boundaries 23a, b. Thus, distance A is preferably equal to or within 10% of the distance measured perpendicularly from weld 20 to each heat affected zone boundary 23a, b.

Lower supports 32a, b extend across lower surface 13 between front and rear surfaces 18, 19 and are oriented parallel to weld 20 and upper supports 31a, b. Lower supports 32a, b are evenly axially spaced (relative to axis 15) to either side of weld 20 by a distance B measured perpendicularly from weld 20. Distance B is greater than distance A previously described, and thus, lower supports 32a, b may be described as being positioned "outside" supports 31a, b relative to weld 20. In this embodiment, lower supports 32a, b are positioned proximal ends 11a, b, respectively. The difference between distance A and distance B defines a distance C equal to the distance measured axially (relative to axis 15) from each upper force transfer member 31a, b to its corresponding lower force transfer member 32a, b on the same side of weld 20. Each force transfer member 31a, 31b, 32a, 32b is configured and arranged to contact sample 10 along a line. Specifically, in this embodiment, each force transfer member 31a, 31b, 32a, 32b is an elongate cylinder that spans the entire width W of sample 10 and is oriented parallel to weld 20.

Referring still to FIG. 2, upper supports 31a, b are positioned between platen 35 and sample 10, and lower supports 32a, b are positioned between a planar lower surface 50 and sample 10. In particular, platen 35 has a planar lower surface 36 that engages and extends axially (relative to axis 15) across both supports 31a, b. Surfaces 36, 50 are rigid, non-deformable surfaces that compress supports 31a, 31b, 32a, 32b and sample 10 therebetween.

Figure 3:
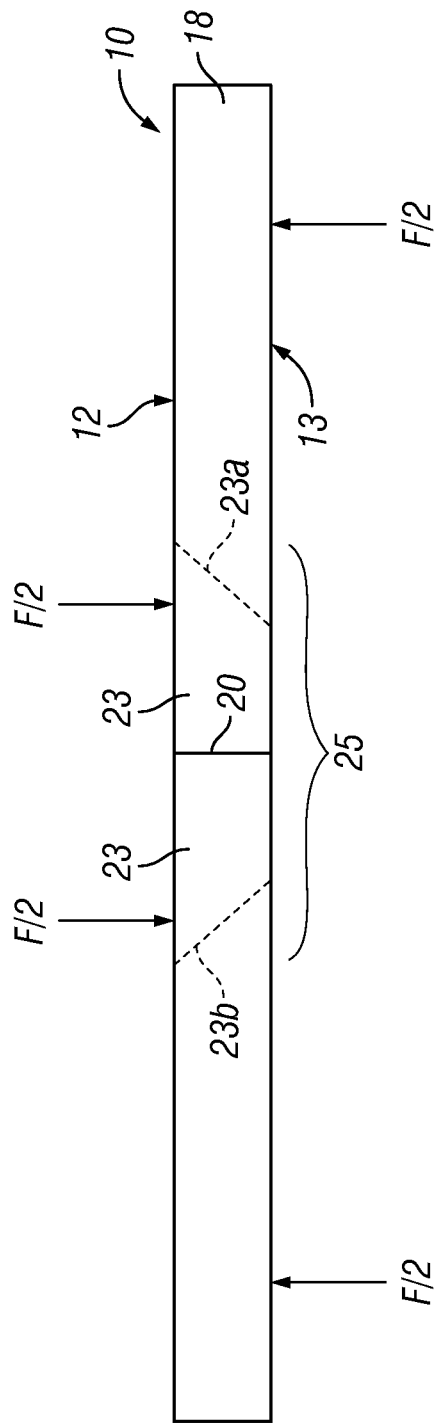
FIG. 3 is a front view of the specimen of FIG. 2 illustrating the forces applied by the four point bending test.

Referring now to FIGS. 2 and 3, planar surfaces 36, 50 are configured to apply loads to sample 10 via supports 31a, 31b, 32a, 32b to generate stresses within sample 10. In general, purely vertical forces are preferred for four point bending tests. Thus, in this embodiment, a vertical downward load F is applied to platen 35. In addition, load F is centered lengthwise and widthwise relative to platen 35. Further, load F is axially centered relative to upper supports 31a,b and lower supports 32a, b, laterally centered between sample sides 18, 19, vertically aligned with weld 20. In other words, a projection of load F passes through weld 20 and is laterally centered between sides 18, 19. Such particular positioning and orientation of load F is preferred as it does not result in the generation of any rotational torques or moments on platen 35 or sample 10.

Load F is transferred through platen 35 to upper surface 12 of sample 10 via upper supports 31a, b. Due to the orientation of applied load F relative to the two supports 31a, b, each force transfer member 31a, b applies one-half of load F to sample 10. The total load F is transferred through sample 10 to lower supports 32a, b and surface 50. However, since lower surface 50 is rigid and non-deformable, it exerts an equal and opposite reactive upward vertical load F that is shared and divided between lower supports 32a, b, and applied to lower surface 13 of sample 10. Thus, when vertical downward load F is applied to platen 35, each upper support 31a, b applies one-half of load F to sample 10, and each lower support 32a, b applies one-half of load F to sample 10 as shown in FIG. 3. Due to the positioning of supports 31a, b and location of application of load F to platen 35, sample 10 is subjected to static conditions (i.e., sample 10 does not experience any moments, torques, or acceleration). Further, since upper supports 31a, b are positioned between lower supports 32a, b, the loads applied to sample 10 by supports 31a, 31b, 32a, 32b seeks to bend or urge ends 11a, b upward relative to area of interest 25, and bend or urge area of interest 25 downward relative to ends 11a, b. As a result, stresses arise within sample 10.

The stresses induced by the four point bending test shown in FIG. 2 and associated loads shown in FIG. 3 include compressive stress parallel to axis 15 in the upper portion of sample 10, and tensile stress parallel to axis 15 in the lower portion of sample 10. The compressive stresses induce compressive strain in the upper portion of sample 10, and the tensile stresses induce tensile strain in the lower portion of sample 10. Without being limited by this or any particular theory, the compressive stress in sample 10 decreases moving perpendicularly downward from upper surface 12, and the tensile stress in sample 10 decreases linearly moving perpendicular upward from lower surface 13. In particular, the compressive stress in sample 10 decreases to zero at a "neutral plane" parallel to and positioned between surfaces 12, 13, and the tensile stress in sample 10 decreases to zero at the neutral plane. Thus, the compressive stress and associated strain in sample 10 are maximum at upper surface 12, and the tensile stress an associated strain in sample 10 are maximum at lower surface 13. The maximum tensile stress in sample 10 during the four point bending test shown in FIGS. 2 and 3 can be calculated according to equation 1 described in more detail below.

Figure 4:
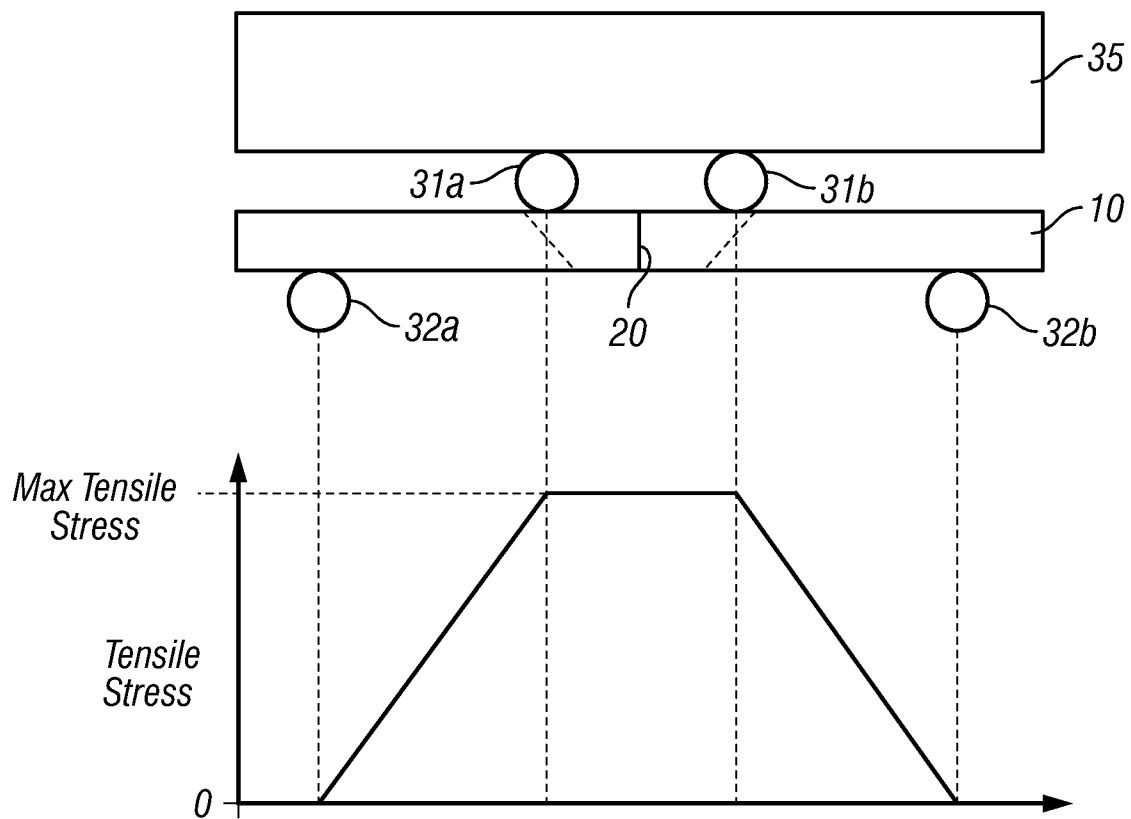
FIG. 4 is a graphical view of the tensile stress distribution along the lower surface of the specimen of FIG. 2 during the four point bending test.

For purposes of SSC testing, the combination of tensile stress and exposure to hydrogen sulfide gas presents the most common failure mode to friction welds, and thus, the tensile stress and strain at lower surface 13 of sample 10 in area of interest 25 are of primary concern and interest. As shown in FIG. 4, the tensile stress in sample 10 at lower surface 13 is constant and at a maximum between supports 31a, b (i.e., in area of interest 25), and tapers off linearly to zero moving axially (relative to axis 15) from support 30a to support 31a and moving axially from support 30b to support 31b. Without being limited by this or any particular theory, and as is known in the art, the maximum tensile stress induced sample 10 at lower surface 13 between supports 31a, b by the four point bending test shown in FIG. 2 may be calculated as follows:

$$S_T = \frac{3CF}{LT^2} \quad \text{(equation 1)}$$

where:
S_T=the maximum tensile stress in sample 10 at lower surface 13 (i.e., between upper supports 31a, b);
C=the distance C between each outer transfer member 32a, b and the nearest inner transfer member 31a, b;
F=the load F applied to the force plate (e.g., platen 35);
L=the length L of sample 10; and
T=the thickness T of sample 10.

Thus, for a given test apparatus (e.g., assembly 30), once distance C, specimen length L, and specimen thickness T are established, a specific tensile stress $S_T$ may be induced in sample 10 at lower surface 13 by simply adjusting the applied load F.

Figure 5:
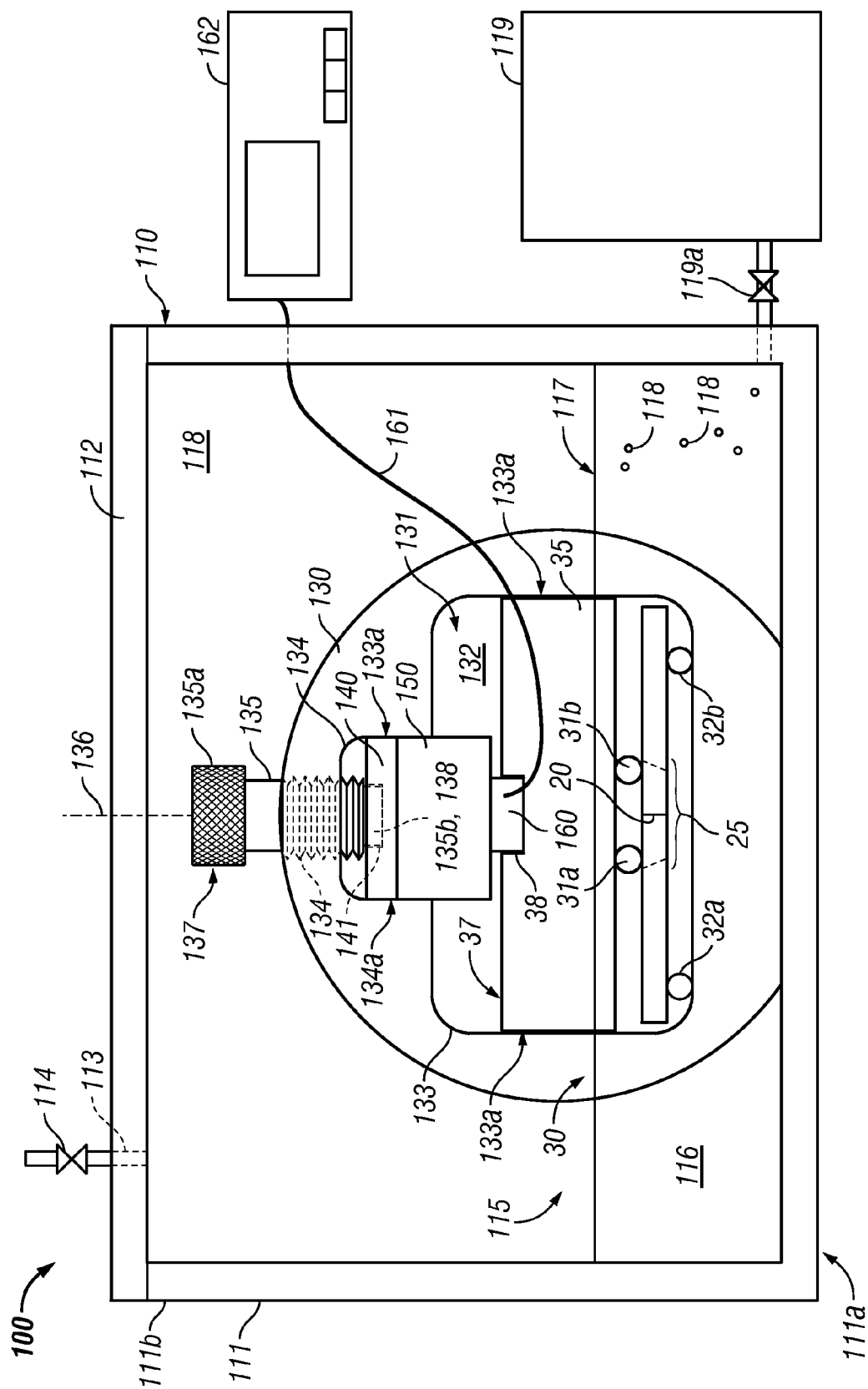
FIG. 5 is a schematic front view of an embodiment of a test apparatus in accordance with the principles described herein.

Referring now to FIG. 5, an embodiment of a testing apparatus 100 for SSC testing a sample with a weld (e.g., sample 10 previously described) is shown. Apparatus 100 includes a testing chamber 110 and a test fixture 120 disposed in testing chamber 110. In this embodiment, testing chamber 110 comprises a generally box-shaped base 111 having an enclosed bottom 111a and an open top 111b, and a removable lid 112 that closes off and seals top 111b. Lid 112 is removed from base 111 to position fixture 120 within testing chamber 110.

In this embodiment, lid 112 includes a vent 113 and a valve 114 that controls fluid flow through vent 113. When valve 114 is open, vent 113 allows fluid communication between the inside and outside of testing chamber 110.

Testing chamber 110 is partially filled with a testing liquid 116 to a liquid level 117, thereby defining a fluid bath 115 within which test fixture 120 is partially disposed. Then, with lid 112 closing off open top 111b of base 111, hydrogen sulfide gas 118 is pumped from a gas tank 119 through a valve 119a into fluid bath 115. Hydrogen sulfide gas 118 bubbles through liquid 116 and fills the portion of testing chamber 110 between liquid level 117 and lid 112. A portion of the hydrogen sulfide gas 118 in testing chamber 110 diffuses into and completely saturates liquid 116. As desired, valve 114 may be opened to bleed remove some of the hydrogen sulfide gas 118 from testing chamber 110 through vent 113. Otherwise, testing chamber 110 is generally maintained at ambient temperature and pressure.

The composition of liquid 116 is preferably selected to be the same or very similar to the downhole liquids expected to contact the welds for which the test is being conducted. Thus, the composition of liquid 116 may be varied for different tests. For example, to SSC test steel welds for use in offshore environments, liquid 116 is preferably sea water or synthetic sea water. Examples of suitable compositions for liquid 116 include, without limitation, an acidified and buffered aqueous brine solution (e.g., 5.0 wt % sodium chloride and 0.5 wt % glacial acetic acid dissolved in distilled or deionized water; 5.0 wt % sodium chloride and 2.5 wt % glacial acetic acid and 0.41 wt % sodium acetate dissolved in distilled or deionized water) and a buffered aqueous brine solution with a chloride content (e.g., distilled or deionized water containing 0.5 g/L sodium acetate and chloride). In addition, to facilitate the sulfide stress cracking phenomenon, liquid 116 preferably has an acidic pH between 2.2 and 6.0.

Figure 6:
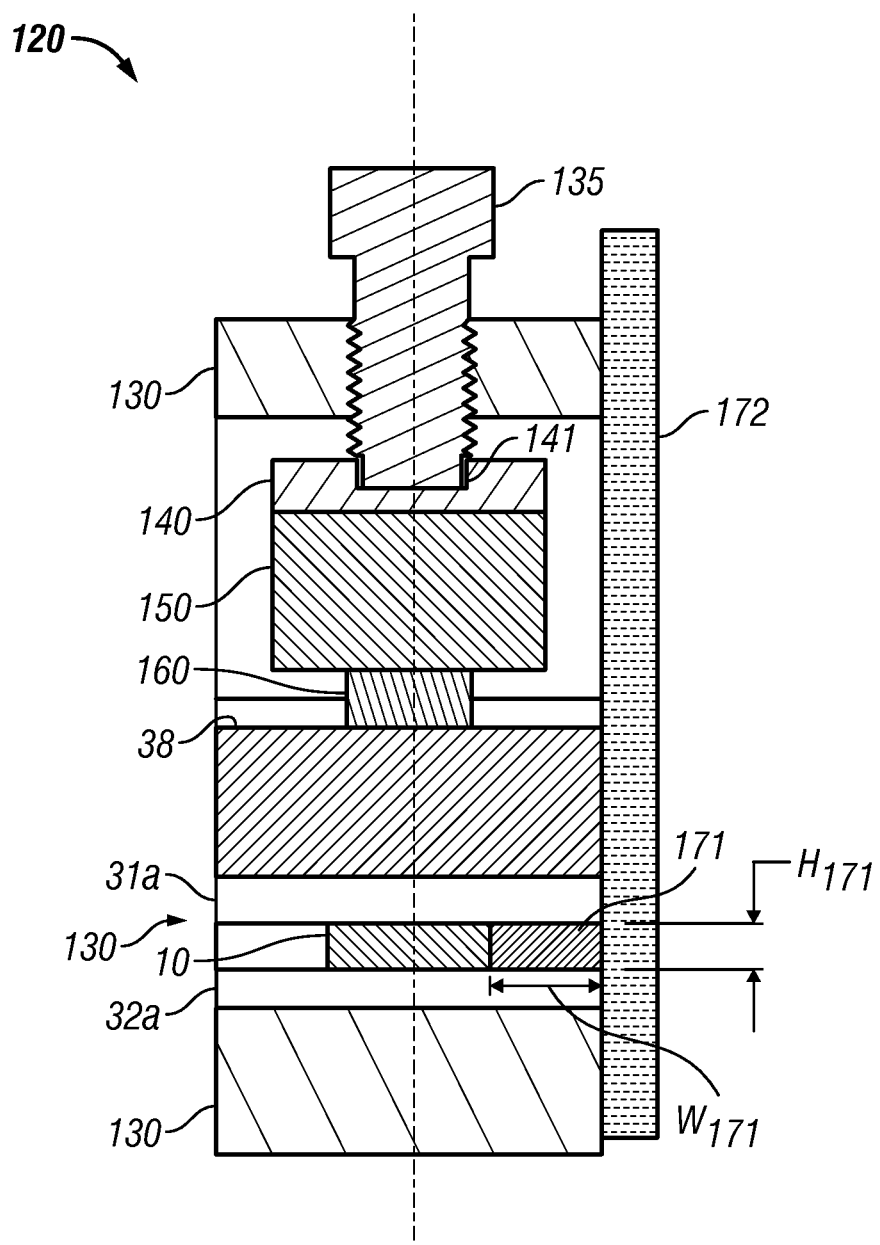
FIG. 6 is a cross-sectional side view of the testing fixture and testing assembly of FIG. 5 illustrating the test specimen being centered relative to the testing fixture for subsequent SSC testing.

Referring now to FIGS. 5 and 6, fixture 120 comprises a housing 130 and four point bending test assembly 30 previously described disposed within housing 130. In particular, housing 130 includes a through passage 131 extending horizontally through housing 130 and defining an internal chamber 132 within housing 130. Since passage 131 extends completely through housing 130, chamber 132 is in fluid communication with liquid 116 and hydrogen sulfide gas 118 in bath 115. Chamber 132 includes a lower portion 133 defined by vertical parallel walls 133a and an upper portion 134 defined by vertical parallel walls 134a extending vertically from lower portion 133. Lower portion 134 is wider than upper portion 134. As will be described in more detail below, test assembly 30 is disposed in chamber lower portion 133.

A load screw 135 is threaded into bore 134 and has a central axis 136, a first or upper end 135a external housing 130, and a second or lower end 135b extending into chamber upper portion 134. In this embodiment, upper end 135a comprises a head 137 having a textured (e.g., knurled) outer surface and lower end 135b comprises a cylindrical tip 138. The textured outer surface of head 137 enhances frictional engagement and gripping of upper end 135a by a tool (e.g., wrench). Load screw 135 is rotated and vertically advanced into and out of bore 134 by applying rotational torque to screw 135 at upper end 135a via head 137.

In general, housing 130 may be made of any suitable material(s), but preferably comprises a durable, rigid material capable of withstanding the loads applied by load screw 135 to test assembly 30, which may exceed 2,000 lbs. Further, since housing 130 is partially submerged in liquid 116, which is saturated with hydrogen sulfide gas 118, housing 130 is preferably made from a low alloy steel that is SSC resistant. In this exemplary embodiment, housing 130 has a cylindrical outer surface with a diameter of about 7.0 inches, and has a wall thickness of about 1.5 inches as measured between the outer and inner surfaces of housing 130.

Test assembly 30 is disposed within chamber lower portion 133 and includes platen 35, upper supports 31a, b, and lower supports 32a, b as previously described with reference to FIG. 2. Test specimen 10 is mounted between upper supports 31a, b and lower supports 32a, b as previously described. The lower surface of chamber 132 is planar and supports lower supports 32a, b in the same manner as surface 50 previously described.

Referring still to FIGS. 5 and 6, in this embodiment, fixture 120 also includes a thrust bearing 140, an upper platen 150, and a load cell 160 arranged in a vertical stack between screw 135 and test assembly 30. As will be described in more detail below, bearing 140, platen 150, and load cell 160 transfer vertical load F applied by load screw 135 to lower platen 35 of test assembly 30. As previously described, application of load F to lower platen 35 subjects sample 10 to a four point bending test and induces internal stresses in sample 10 (e.g., tensile stress in sample 10 at lower surface 13). To minimize and/or eliminate the application of any rotational moments to sample 10, upper portion 134, lower portion 133, thrust bearing 140, upper platen 150, load cell 160, lower platen 35, and sample 10 are configured, sized, and positioned such that each is centered relative to load screw 135 within housing 130. In other words, a projection of load screw axis 136 passes vertically through the center of bearing 140, upper platen 150, load cell 160, lower platen 35, and sample 10 in top view.

As best shown in FIG. 6, in this embodiment, sample 10 is centered within housing 130 with a centering assembly 170 including an elongate alignment member 171 and an alignment plate 172. Alignment member 171 is a rectangular beam that has a height $H_{171}$ less than height H of sample 10 and a length equal to length L of sample 10. Alignment member 171 is placed between upper supports 31a, b and lower supports 32a, b and bears against side surface 19 of sample 10. Alignment plate 172 is used to urge alignment member 171 and sample 10 through internal chamber 132 until sample 10 is centered within fixture 120 and housing 130. Specifically, alignment plate 172 has a width $W_{171}$ selected such that sample 10 is centered within fixture 120 and housing 130 when alignment plate 172 comes into contact with the back of housing 130. Once sample 10 is centered, alignment plate 172 may be withdrawn from housing 130 and alignment member 171 may be removed from chamber 132.

Referring again to FIGS. 5 and 6, lower end 135b of load screw 135 bears against thrust bearing 140. In this embodiment, the upper surface of thrust bearing 140 includes a cylindrical recess 141 that slidingly receives cylindrical tip 138 of screw 135. Tip 138 has an outer diameter that is substantially the same or slightly less than the diameter of recess 141, thereby restricting and/or preventing thrust bearing 140 from pivoting or moving translationally relative to tip 138 and load screw 135. Such mating engagement of screw tip 138 and bearing recess 141 helps maintain the vertical alignment of loading screw 135 relative to thrust bearing 140, thereby reducing the likelihood of generating rotational moments that could unevenly load test assembly 30. Further, in this embodiment, thrust bearing 140 and upper platen 150 are disposed within chamber upper portion 134 and slidingly engage vertical internal walls 134a defining chamber upper portion 134. Thus, as screw tip 137 engages and is rotated relative to thrust bearing 140 about axis 136, walls 134a simultaneously prevent thrust bearing 140 and upper platen 150 from rotating along with screw 135 and guide the vertical movement of bearing 140 and upper platen 150 within upper portion 134.

Load cell 160 is positioned between platens 35, 150, and transfers and measures vertical loads therebetween. An electrical conductor 161 couples load cell 160 to an output device 162 that displays the vertical force measured by load cell 160. In general, load cell 160 may comprise any suitable load cell capable of measuring the applied linear loads. Load cell 160 is preferably positioned above fluid level 117 so that it is not harmed by the corrosive fluids in bath 111.

In this embodiment, lower platen 35 has an upper surface 37 including a recess 38 centered relative to screw axis 136, vertically aligned with weld 20, and centered between supports 31a, b. Load cell 160 is seated in recess 38, which aligns load cell 160 within fixture 120 and provides an opening for wire 161 to exit fixture 120 in route to output device 162. Load cell 160 has an outer diameter that is substantially the same or slightly less than the width of recess 38, thereby restricting and/or preventing lower platen 35 from pivoting or rotating relative to load cell 160. Such mating engagement of load cell 160 and platen recess 38 helps maintain the vertical alignment of load cell 160 relative to lower platen 35, thereby reducing the likelihood of generating rotational moments that could unevenly load test assembly 30. Further, in this embodiment, lower platen 35 slidingly engage vertical internal walls 133a defining chamber lower portion 133. Thus, walls 132a guide the vertical movement of lower platen 35.

To apply load F to platen 35 for SSC testing of weld 20 and area of interest 25 of sample 10, load screw 135 is rotated and advanced through housing bore 134 and into engagement with thrust bearing 140. With screw tip 138 seated in bearing recess 141, continued rotation and advancement of screw 135 applies a vertically downward load F on thrust bearing 140. It should be appreciated that application of load F by rotation of screw 135 allows for smooth, controlled application and variation of load F. Rotation of screw 135 is achieved by application of rotational torque to head 137, which may performed with a hand wrench. Thrust bearing 140 transfers load F to platen 140, which transfers load F through load cell 160 to lower platen 35 and testing assembly 30. Thus, in this embodiment, two platens 35, 150 are employed to transfer vertical load F to testing assembly 30.

Apparatus 100 includes several features that offer the potential to maintain purely vertical loads on sample 10 during application of load F, thereby enabling uniform, consistent application of forces to sample 10, and minimizing and/or eliminating the application of rotational moments to sample 10. Such features include the vertical alignment of screw 135, thrust bearing 140, platens 150, 35, load cell 160 and testing assembly 30; the mating engagement of tip 138 and bearing recess 141; the mating engagement of load cell 160 with platen recess 38; the sliding engagement of bearing 140 and upper platen 150 with housing walls 134a; the sliding engagement of lower platen 35 with housing walls 133a; and the centering of bearing 140, platens 35, 150, load cell 160, and sample 10 relative to screw axis 136 and fixture 120.

In the manner described, vertical load F is applied to testing assembly 30 to place sample 10 in a four point bending test and induce internal stresses in sample 10. During application of load F, load cell 160 and output device 162 enable real time measurement and monitoring of the actual value of load F and the ongoing SSC test to alert the operator of a failure (specimen cracking or fracture). In addition, load cell 160 enables accurate, precise control of the load F and associated stress induced in the sample (e.g., sample 10) during SSC testing with apparatus 100.

As previously described, the particular load F necessary to achieve a desired stress in sample 10 at lower surface 13 may be calculated. Depending on the desired stress and corresponding load F (necessary to achieve the desired stress), screw 135 may be smoothly and controllably rotated in a first direction to increase load F and rotated in a second direction opposite the first direction to decrease load F. Thus, fixture 120 enables controlled application of load F and inducement of stress to sample 10. Further, load F and associated stresses induced in sample 10 can be maintained constant in a particular region of sample 10 (e.g., area of interest 25 and weld 20) for an extended period of time.

In some conventional bent-beam tests, the induced stress is calculated based on the measurements of sample bending or deflection. Consequently, the samples used in such tests are typically thin (e.g., 0.062 inches thick) in order to exhibit a sufficiently large deflection that can be measured accurately. However, inclusion of load cell 160 enables simple calculation of the induced stress without the need to accurately measure deflection or bending, thereby eliminating the need for thin specimen. Without being limited by this or any particular theory, as compared to thin testing samples, thicker testing samples more accurately reflect the behavior of welds in downhole equipment used in the field.

During application of load F, test assembly 30 and sample 10 are positioned below fluid level 117, and thus, are exposed to liquid 116 and hydrogen sulfide gas 118. Thus, sample 10, weld 20, and area of interest 25 are simultaneously subjected to hydrogen sulfide gas 118 and stress for SSC testing. In general, sample 10 may be SSC tested with apparatus 100 for any desired period of time. However, consistent with other standardized SSC testing standards, sample 10, weld 20, and area of interest 25 are preferably tested for a period of 30 days.

In this embodiment, apparatus 100 does not include any strain gages mounted to sample 10, however, in other embodiments, one or more electronic strain gages are affixed to the sample (e.g., sample 10) to measure and monitor stress induced in the sample.

As previously shown and described, testing sample 10 is a rectangular bar having orthogonal, planar surfaces. However, in the field, the downhole steel tubulars subjected to stress and hydrogen sulfide gas have a cylindrical geometries. Thus, an SSC test specimen or sample that includes a cylindrical surface offers the potential to more accurately reflect the effects of SSC on downhole tubulars and associated welds.

Figure 7:
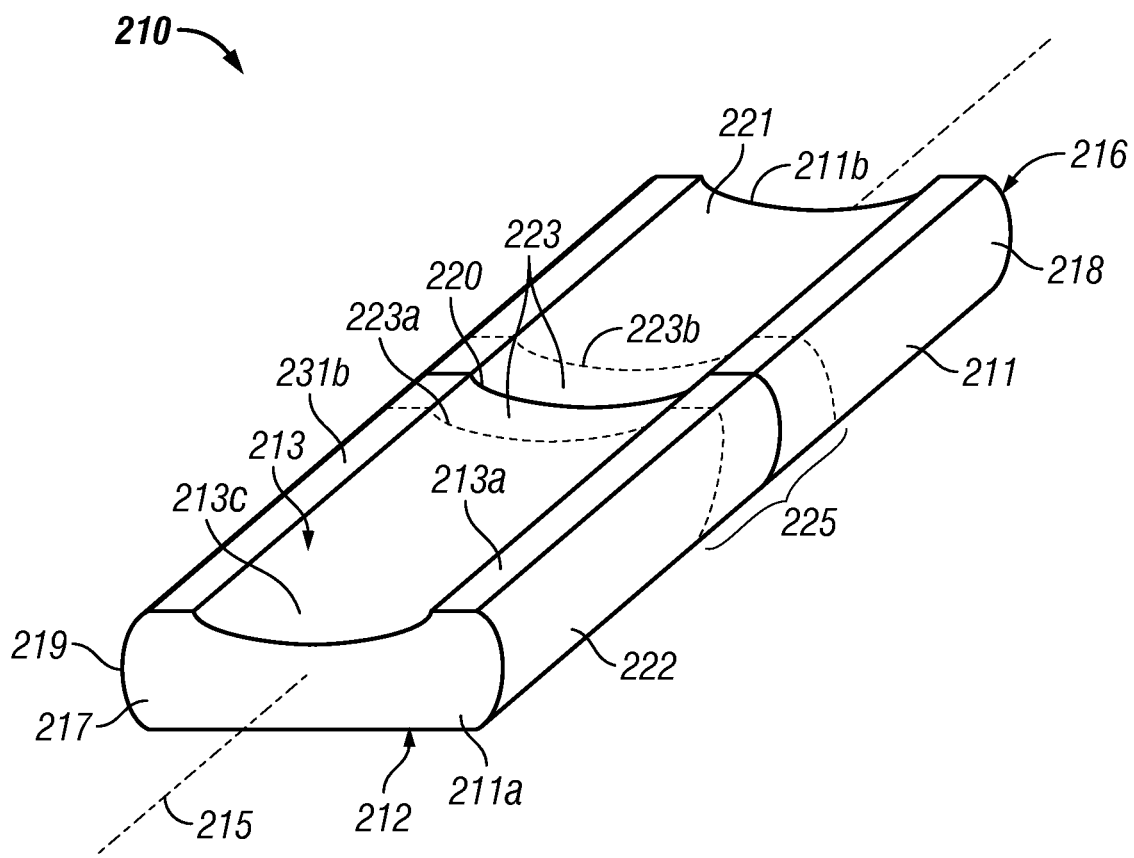
FIG. 7 is a perspective view of an embodiment of a welded specimen for SSC testing.
Figure 8:
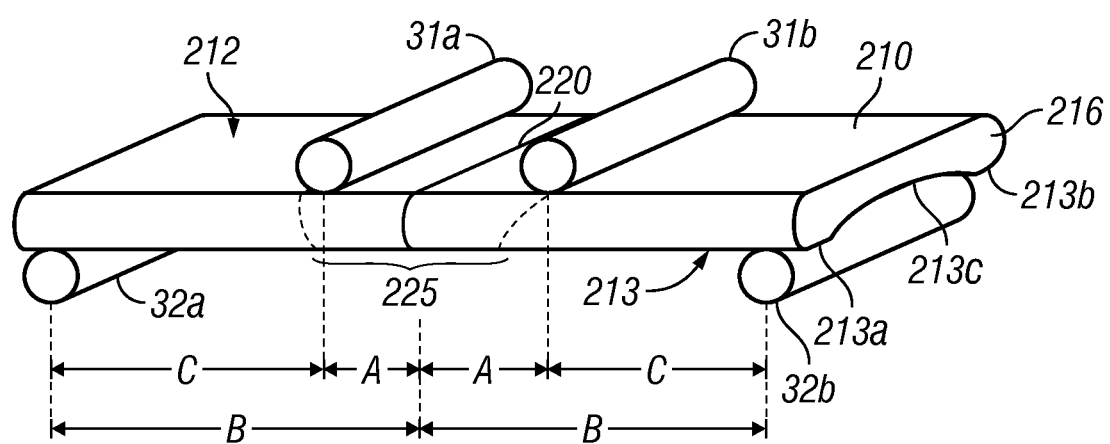
FIG. 8 is a perspective view of the specimen of FIG. 7 mounted between the upper and lower supports of the testing assembly of FIG. 5.
Figure 9:
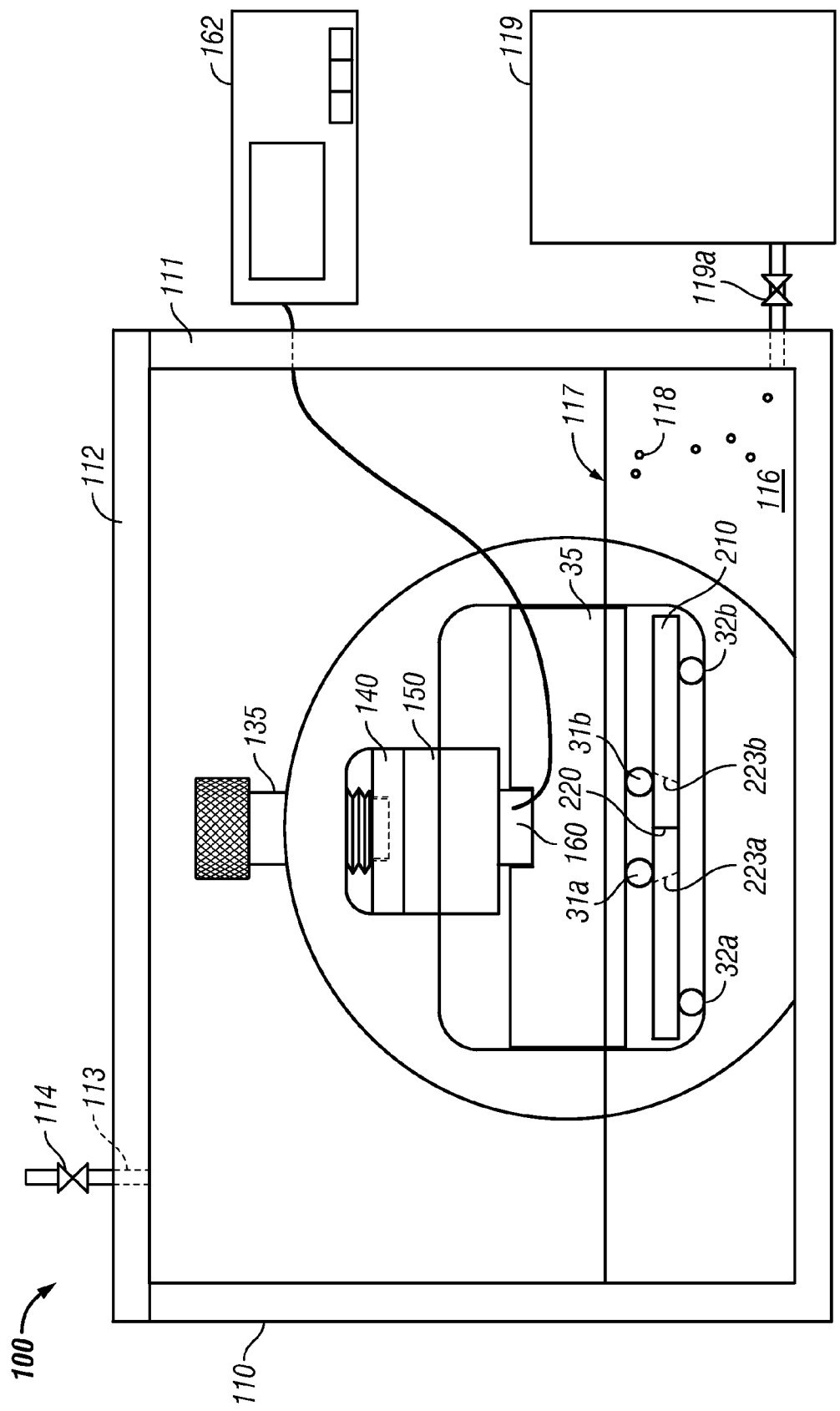
FIG. 9 is a schematic front view of the specimen of FIG. 7 mounted in the test apparatus of FIG. 5.

Referring now to FIG. 7, an embodiment of a test specimen or sample 210 that offers the potential to more accurately reflects tubular weld performance in the field is shown. In FIG. 7, sample 210 is shown upside down to highlight the features on the lower surface of sample 210. FIG. 8 illustrates the preferred orientation of sample 210 mounted between upper and lower supports 31a, b, 32a, b, respectively, of test assembly 30 previously described, and FIG. 9 illustrates sample 210 being subjected to SSC testing with test apparatus 100 previously described.

As shown in FIG. 7, sample 210 has an elongate body 211 with a central or longitudinal axis 215, a first end 211a and a second end 211b opposite first end 211a. In addition, body 211 has a planar upper surface 212 extending between ends 211a, b, a lower surface 213 extending between ends 211a, 2b, planar end surfaces 216, 217 extending vertically between upper and lower surfaces 212, 213 at ends 211a, b, respectively, and lateral or side surfaces 218, 219, respectively, extending between upper and lower surfaces 212, 213.

Similar to sample 10 previously described, sample 210 is formed from a first component 221 axially abutting and welded end-to-end to a second component 222 with a friction weld 220. Components 221, 222, and hence sample 210, are made from a material for which weld SSC testing is desired (e.g., steel). A heat affected zone 223 extends the length of friction weld 220 and immediately surrounds friction weld 220. Heat affected zone boundaries 223a, b define the extent to which heat affected zone 223 extends from weld 220. Together, friction weld 220 and heat affected zone 223 define an area of interest 225 in sample 210 to be SSC tested.

Unlike sample 10 previously described, lower surface 213 and side surfaces 218, 219 of sample 210 are not planar. Specifically, in this embodiment, lower surface 213 includes a first lateral or outer section 213a, a second lateral or outer section 213b, and an intermediate section 213c positioned between sections 213a, b. Each section 213a, b, c extends axially (relative to axis 215) between ends 211a, b. In addition, first lateral section 213a extends between intermediate section 213c and side surface 218, and second lateral section 213b extends between intermediate section 213c and side surface 219. In this embodiment, each lateral section 213a, b of lower surface 213 is planar, however, intermediate section 213c of lower surface 213 is arcuate. In particular, intermediate section 213c is concave and cylindrical. In this embodiment, intermediate section 213c has a constant radius of curvature. In this embodiment, the radius of intermediate section 213c of lower surface 213 is sufficiently large that it has little to no impact on the maximum tensile stress calculations. In other words, even though sample 210 does not have a uniform thickness (due to the curvature of intermediate section 213c), equation 1 previously discussed may still be used to calculate the maximum tensile stress induced in sample 210 at lower surface 213. Each side surface 218, 219 extends axially (relative to axis 215) between ends 211a, b. In addition, side surfaces 218, 219 extends between upper surface 212 and lower surface sections 213a, b, respectively. In this embodiment, each side surface 218, 219 is convex.

Side sections 213a, b of lower surface 213 are flattened to reduce the likelihood of stress concentrations when sample 210 is mounted in testing assembly 30 previously described and lower supports 32a, b bear against sections 213a, b. In addition, the intersection of each side section 213a, b with intermediate section 213c is rounded or radiused to reduce stress concentrations, and the intersection of each side section 213a, b with its corresponding side surface 218, 219, respectively, is rounded or radiused to reduce stress concentrations. Rounding the intersections between each side section 213a, b with its corresponding side surface 218, 219, respectively, also limits hydrogen access and diffusion to a single surface as opposed to two distinct intersecting surfaces.

Referring now to FIGS. 8 and 9, sample 210 is mounted in test assembly 30 and SSC tested in apparatus 100 in the same manner as sample 10 previously described. Namely, sample 210 is mounted between upper supports 31a, b and lower force supports 32a, b. Sample alignment assembly 170 previously described may be used to center sample 210 relative to screw 135 and housing 130. Supports 31a, b extend across upper surface 212 between surfaces 218, 219. Upper surface 212 is planar, so each support 31a, b continuously contacts surface 212 between side surfaces 218, 218. In addition, supports 31a, b are oriented parallel to friction weld 220 and are evenly spaced to either side of weld 220 by distance A measured perpendicularly from weld 220. Distance A is equal to or within 10% of the distance measured perpendicularly from weld 220 to the boundary of heat affected zone 223. Thus, supports 31a, b are positioned to extend along heat affected zone boundaries 223a, b, respectively.

Lower supports 32a, b extend across lower surface 213 between side surfaces 218, 219 and are oriented parallel to friction weld 220. Supports 32a, b engage planar lateral sections 213a, b of lower surface 213, but do not contact intermediate cylindrical section 213c since it is recessed relative to surfaces 213a, b. Supports 32a, b are evenly spaced to either side of weld 220 by lateral distance B measured perpendicularly from weld 220. Distance B is greater than distance A.

Supports 31a, b apply forces to sample 210 along upper surface 212, and lower supports 32a, b apply forces to sample 210 along lower surface sections 213a, b. In this embodiment, the primary focus of the SSC test is area of interest 225 along the curved, cylindrical intermediate section 213c of lower surface 213.

During application of a load F applied by load screw 135, test assembly 30 and sample 210 are positioned below fluid level 117, and thus, are exposed to liquid 116 and hydrogen sulfide gas 118. Thus, sample 210, weld 220, and area of interest 225 are simultaneously subjected to hydrogen sulfide gas 118 and stress for SSC testing. In general, sample 210 may be SSC tested with apparatus 100 for any desired period of time. However, consistent with other standardized SSC testing standards, sample 210, weld 220, and area of interest 225 are preferably tested for a period of 30 days.

In the manner described, embodiments of testing apparatus 100 provide a system for use in SSC 30-day corrosion testing of steel welds (e.g., friction welds). Such testing assures the steel welds can survive under a prescribed stress in a liquid environment with hydrogen sulfide gas exposure for a duration of at least 30 days. In addition, embodiments of apparatus 100 provide a relatively simple, low cost, easy to use system for frequent and/or repeated testing of welds and associated heat affected zones.

While preferred embodiments have been shown and described, modifications thereof can be made by one skilled in the art without departing from the scope or teachings herein. The embodiments described herein are exemplary only and are not limiting. Many variations and modifications of the systems, apparatus, and processes described herein are possible and are within the scope of the invention. For example, the relative dimensions of various parts, the materials from which the various parts are made, and other parameters can be varied. Accordingly, the scope of protection is not limited to the embodiments described herein, but is only limited by the claims that follow, the scope of which shall include all equivalents of the subject matter of the claims.

What is claimed is:

1. A system for sulfide stress cracking testing, comprising:
   an enclosed testing chamber including a fluid bath comprising a liquid saturated with hydrogen sulfide gas;
   a test fixture disposed in the testing chamber and at least partially submerged in the fluid bath, wherein the test fixture includes a housing having an internal chamber in fluid communication with the fluid bath and a test assembly disposed in the internal chamber;
   wherein the test assembly comprises:
      a first upper support and a second upper support;
      a first lower support and a second lower support; and
      a first platen engaging each of the upper supports and adapted to transfer an applied vertical load to the upper supports;
      a second platen disposed in the internal chamber of the housing above the first platen, wherein the second platen slidingly engages a pair of opposed vertical internal walls of the housing and is configured to transfer the applied vertical load to the first platen;
      a test specimen mounted in the test assembly between the upper supports and the lower supports, the upper supports engaging an upper surface of the test specimen and the lower supports engaging a lower surface of the test specimen;

wherein the test specimen has a longitudinal axis, a first end, a second end opposite the first end, and includes a weld and a heat affected zone axially disposed between the first end and the second end;

wherein the first upper support is axially positioned between the weld and the first end and the second upper support is axially positioned between the weld and the second end;

wherein the first lower support is axially positioned between the first upper support and the first end and the second lower support is axially positioned between the second upper support and the second end.

2. The system of claim 1, wherein the first upper support and the second upper support are evenly axially spaced from the weld, and wherein the first lower support and the second lower support are evenly axially spaced from the weld.

3. The system of claim 2, wherein the heat affected zone has a first boundary axially disposed between the weld and the first end and a second boundary axially disposed between the weld and the second end;

wherein the first upper support is positioned along the first boundary of the heat affected zone and the second upper support is positioned along the second boundary of the heat affected zone.

4. The system of claim 3, wherein the weld is a friction weld.

5. The system of claim 1, further comprising a load cell disposed in the internal chamber of the housing, wherein the load cell is positioned between the first platen and the second platen and is adapted to measure the applied vertical load.

6. The system of claim 5, wherein the first platen has an upper surface including a recess and wherein the load cell is seated in the recess.

7. The system of claim 5, further comprising a thrust bearing engaging the second platen and a load screw threadably engaging a throughbore in the housing;

wherein the load screw has a first end external the housing and a second end extending into the internal chamber of the housing and engaging the thrust bearing.

8. The system of claim 7, wherein the second end of the load screw engages a mating recess in an upper surface of the thrust bearing.

9. The system of claim 8, wherein the second end of the load screw comprises a cylindrical tip that mates with the recess.

10. The system of claim 7, wherein the thrust bearing slidingly engages the housing.

11. The system of claim 5, further comprising an output device adapted to display the applied force measured by the load cell.

12. The system of claim 1, wherein the test specimen includes a first side surface extending from the lower surface to the upper surface and a second side surface opposite the first side surface and extending from the lower surface to the upper surface;

wherein the lower surface includes a first planar section that extends axially from the first end to the second end and intersects the first side surface, a second planar section that extends axially from the first end to the second end and intersects the second side surface, and an intermediate section disposed between the first planar section and the second planar section; and wherein the intermediate section of the lower surface is a cylindrical surface extending from the first end to the second end.

13. The system of claim 12, wherein an intersection between the first planar section of the lower surface and the first side surface is radiused, and an intersection between the second planar section of the lower surface and the second side surface is radiused.

14. The system of claim 1, wherein the housing is made from a material that is hydrogen sulfide corrosion resistant.

15. A method for corrosion testing a weld, comprising:
(a) providing a test specimen having a longitudinal axis, a first end, a second end opposite the first end, and a weld axially positioned between the first end and the second;
(b) mounting the test specimen between a pair of upper supports and a pair of lower supports;
(c) subjecting the test specimen to a four point bending test with the upper supports and the lower supports to induce tensile stress in the specimen along a lower surface of the specimen during;
(d) measuring the applied load with a load cell; and
(e) exposing the weld to hydrogen sulfide gas during (c);
wherein the weld is a friction weld;
wherein (c) further comprises:
 (c1) applying a vertical load to the upper supports with a first platen;
 (c2) applying the vertical load to the first platen with a second platen, wherein
the load cell is positioned between the first platen and the second platen.

16. The method of claim 15, further comprising:
flowing the hydrogen sulfide gas through a liquid in a liquid bath;
submerging the test specimen in the liquid bath.

17. The method of claim 15, further comprising (f) continuously performing (c) and (d) for at least 30 days.

18. The method of claim 15, wherein the lower surface of the test specimen includes a cylindrical surface before subjecting the test specimen to the four-point bending test in (c).

19. The method of claim 18, wherein the cylindrical surface is a concave surface extending from the first end to the second end of the test specimen.

* * * * *